United States Patent
Schindler et al.

(10) Patent No.: US 6,344,468 B1
(45) Date of Patent: Feb. 5, 2002

(54) SUBSTITUTED ISOINDOLONES AND THEIR USE AS CYCLIC GMP MODULATORS IN MEDICAMENTS

(75) Inventors: Ursula Schindler, Bad Soden; Karl Schoenafinger, Alzenau; Hartmut Strobel, Liederbach, all of (DE); Viola Groehn, Neuhausen (CH)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 09/622,691

(22) PCT Filed: Feb. 12, 1999

(86) PCT No.: PCT/EP99/00931

§ 371 Date: Oct. 6, 2000

§ 102(e) Date: Oct. 6, 2000

(87) PCT Pub. No.: WO99/42444

PCT Pub. Date: Aug. 26, 1999

(30) Foreign Application Priority Data

Feb. 21, 1998 (DE) .......................... 198 07 423

(51) Int. Cl.$^7$ ................ A61K 31/4035; C07D 209/48; C07D 401/04; C07D 409/04

(52) U.S. Cl. ................ 514/339; 514/414; 514/416; 546/277.1; 548/466; 548/472

(58) Field of Search ................ 514/339, 414, 514/416; 546/277.1; 548/466, 472

(56) References Cited

U.S. PATENT DOCUMENTS 5,869,516 A   2/1999   Arlt et al. .................. 514/404

FOREIGN PATENT DOCUMENTS

| EP | 0 667 345 | 8/1995 |
| EP | 0 743 304 A1 | 11/1996 |

OTHER PUBLICATIONS

Nishio et al., Journal of Heterocyclic Chemistry, 32(3), 883–891, 1995.*
Vesely, D.L., "B Complex Vitamins Activate Rat Guanylate Cyclase and Increase Cyclic GMP Levels", European Journal of Clinical Investigation, 15, pp. 258–262 (1985).
Vesely, D.L., "Phencyclidine Stimulates Guanylate Cyclase Activity", Biochemical and Biophical Research Communications, vol. 88, No. 4, pp. 1244–1248, (1979).
Ignarro, L.J., "Regulation of Cytosolic Guanylyl Clyclase by Porphyrins and Metalloporphyrins", Advances in Pharmacology, vol. 26, pp. 35–65, (1994).
Pettibone, D.J. , et al., "Structurally Novel Stimulator of Guanylate Cyclase with Long–Lasting Hypotensive Activity in the Dog", European Journal of Pharmacology, 116, pp. 307–312, (1985).

Yu, S.M., et al., "Vasorelaxant Effect of Isoliquiritgenin, a Novel Soluble Guanylate Cyclase Activator, in Rat Aorta", British Journal of Pharmacology, 114, pp. 1587–15945, (1995).
Ko, F.N., et al., "YC–1 a Novel Activator of Platelet Guanylate Cyclase", Blood, vol. 84, No. 12, pp., 4226–4233 (1994).
Yu, S.M., et al., "Mechanism of Anti–Proliferation Caused by YC–1, an Indazole Derivative in Cultured Rat A10 Vascular Smooth–Muscle Cells", Biochem. J., 306, pp. 787–792, (1995).
Wu, C.C., et al., "YC–1 Inhibited Human Platelet Aggregation Though NO–Independent Activation of Soluble Guanylate Cyclase", British Journal of Pharmacology, 116, pp. 1973–1978, (1995).
Winn, M., et al., "Intramolecular Amidoalkylations at Carbon. Synthesis of Heterocyclic Amines", The Journal of Organic Chemistry, vol., 33, No. 10, pp., 3779–3783, (1968).
Delcey, M.C., et al., "Synthesis of 1–Substituted 3,4–Diarylisoquinoline Derivatives", Heterocyles, vol. 41, No. 8, pp. 1721–1730, (1995).
Bahajaj, A.A., et al., "Formation of Spiro Indane Derivatives from Hydroxy Lactams Derived from N–(1–Phenylethyl)–Phthalimide and –Pyridine–2, 3–dicarboximide", J. Chem. Soc. Perkin Trans., 1, pp. 1041–1046, (1996).

(List continued on next page.)

Primary Examiner—Fiona T. Powers
(74) Attorney, Agent, or Firm—Finnegan, Henderson, Farabow, Garrett & Dunner, LLP

(57) ABSTRACT

The present invention relates to substituted isoindolone derivatives of the formula I,

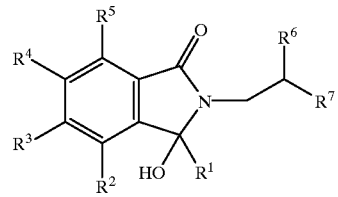

I in which $R^1$, $R^2$, $R^3$, $R^4$, $R^5$, $R^6$ and $R^7$ are as defined in the claims, which are useful pharmaceutically active compounds for the therapy and prophylaxis of illnesses, for example cardiovascular diseases such as hypertension, angina pectoris, cardiac insufficiency, thromboses or atherosclerosis. The compounds of the formula I are capable of modulating the body's production of cyclic guanosine monophosphate (cGMP) and are generally suitable for the therapy and prophylaxis of illnesses which are associated with a disturbed cGMP balance. The invention furthermore relates to processes for preparing compounds of the formula I, to their use for the therapy and prophylaxis of the abovementioned illnesses and for preparing pharmaceuticals for these, and also pharmaceutical preparations which comprise compounds of the formula I.

14 Claims, No Drawings

OTHER PUBLICATIONS

Boykin, D.W., et al., "Synthesis of Bis–2,7–Substitude 1,2,3,6,7,8–Hexahdroisoindolo[5,6–f]isoindole–1,2,3,6,8–tetraones", J. Heterocyclic Chem., 28, pp. 609–611, (1991).

Wanag, G., "Kondensation Primärer Di–und Polyamine mit Phthalsäureanhydrid in Eisessig", Chem. Ber., 75 pp. 719–725, (1942).

* cited by examiner

SUBSTITUTED ISOINDOLONES AND THEIR USE AS CYCLIC GMP MODULATORS IN MEDICAMENTS

This application is a national stage filing under 35 U.S.C. § 371 of international application No. PCT/EP99/00931, filed on Feb. 12, 1999.

The present invention relates to substituted isoindolone derivatives of the formula I,

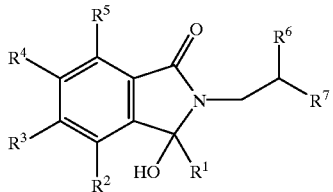

in which $R^1$, $R^2$, $R^3$, $R^4$, $R^5$, $R^6$ and $R^7$ are as defined below, which are useful pharmaceutically active compounds for the therapy and prophylaxis of illnesses, for example cardiovascular diseases such as hypertension, angina pectoris, cardiac insufficiency, thromboses or atherosclerosis. The compounds of the formula I are capable of modulating the body's production of cyclic guanosine monophosphate (cGMP) and are generally suitable for the therapy and prophylaxis of illnesses which are associated with a disturbed cGMP balance. The invention furthermore relates to processes for preparing compounds of the formula I, to their use for the therapy and prophylaxis of the abovementioned illnesses and for preparing pharmaceuticals for these, and also pharmaceutical preparations which comprise compounds of the formula I.

cGMP is an important intracellular messenger which triggers a number of pharmacological effects via the modulation of cGMP-dependent protein kinases, phosphodiesterases and ion channels. Examples are the relaxation of smooth muscles, the inhibition of thrombocyte activation and the inhibition of the proliferation of smooth-muscle cells and leukocyte adhesion. cGMP is produced by particulate and soluble guanylate cyclases (GC) as a response to a number of extra- and intracellular stimuli. In the case of the particulate guanylate cyclases, stimulation is essentially effected by peptidic messengers, such as the atrial natriuretic peptide or the cerebral natriuretic peptide. The soluble guanylate cyclases (sGC), which are cytosolic heterodimeric hem proteins, in contrast, are essentially regulated by a family of low-molecular-weight factors which are formed enzymatically. The most important stimulant is nitrogen monoxide (NO) or a closely related species. The function of other factors such as carbon monoxide or the hydroxyl radical is still largely unclear. Binding of NO to the hem with formation of a penta-coordinate hem-nitrosyl complex is being discussed as activation mechanism of the activation by NO. The associated release of the histidine which is bound in the basal state to the iron converts the enzyme into the active conformation.

Active soluble guanylate cyclases are in each case composed of an α and a β subunit. Several subunit subtypes have been described which differ from one another with respect to sequence, tissue-specific distribution and expression in different development stages. The subtypes $\alpha_1$ and $\beta_1$ are mainly expressed in brain and lung, while $\beta_2$ is found in particular in liver and kidney. The subtype $\alpha_2$ was demonstrated in human fetal brain. The subunits referred to as $\alpha_3$ and $\beta_3$ were isolated from human brain and are homologous to $\alpha_1$ and $\beta_1$. More recent works indicate an $\alpha_{2i}$ subunit which contains an insert in the catalytic domain. All subunits show great homologies in the region of the catalytic domain. The enzymes presumably contain one hem per heterodimer, which is bound via $\beta_1$-Cys-78 and/or $\beta_1$-His-105 and is part of the regulatory center.

Under pathologic conditions, the formation of guanylate-cyclase-activating factors can be reduced, or their degradation may be promoted owing to the increased occurrence of free radicals. The resulting reduced activation of the sGC leads, via a weakening of the respective cGMP-mediated cellular response, for example to an increase in the blood pressure, to platelet activation or to increased cell proliferation and cell adhesion. As a consequence, formation of endothelial dysfunction, atherosclerosis, hypertension, stable and unstable angina pectoris, thromboses, myocardial infarction, strokes or erectile dysfunction results. Pharmacological stimulation of sGC offers a possibility to normalize cGMP production and therefore makes possible the treatment and prevention of such disorders.

For the pharmacological stimulation of sGC, use has hitherto almost exclusively been made of compounds whose activity is based on an intermediate NO release, for example organic nitrates. The drawback of this treatment is the development of tolerance and a reduction of activity, and the higher dosage which is required because of this.

Various sGC stimulators which do not act via NO release were described by Vesely in a relatively large number of works. However, the compounds, most of which are hormones, plant hormones, vitamins or, for example, natural compounds such as lizard poisons, generally only have weak effects on the cGMP formation in cell lysates (D. L. Vesely, Eur. J. Clin. Invest. 15 (1985) 258; D. L. Vesely, Biochem. Biophys. Res. Comm. 88 (1979) 1244). A stimulation of hem-free guanylate cyclase by protoporphyrin IX was demonstrated by Ignarro et al. (Adv. Pharmacol. 26 (1994) 35). Pettibone et al. (Eur. J. Pharmacol. 116 (1985) 307) described an antihypertensive action of diphenyliodonium hexafluorophosphate and attributed this to a stimulation of sGC. According to Yu et al. (Brit. J. Pharmacol. 114 (1995) 1587), isoliquiritigenin, which has a relaxing action on isolated rat aortas, also activates sGC. Ko et al. (Blood 84 (1994) 4226), Yu et al. (Biochem. J. 306 (1995) 787) and Wu et al. (Brit. J. Pharmacol. 116 (1995) 1973) demonstrated an sGC-stimulating activity of 1-benzyl-3-(5-hydroxymethyl-2-furyl)-indazole and demonstrated an antiproliferative and thrombocyte-inhibiting action. EP-A-667 345 describes various indazoles as inhibitors of thrombocyte aggregation.

Various nitrogen-substituted 3-hydroxyisoindol-1-ones are known. In J. Org. Chem. 33 (1968) 3779, Winn and Zaugg describe the compounds of the formula I in which $R^1$ is unsubstituted phenyl, $R^2$, $R^3$, $R^4$, $R^5$ and $R^7$ are hydrogen and $R^6$ is unsubstituted phenyl or 3,4-dimethoxyphenyl. However, they do not report on any pharmacological activity of the compounds. Surprisingly, it has now been found that the compounds of the formula I according to the invention effect a strong activation of guanylate cyclase, owing to which they are suitable for the therapy and prophylaxis of diseases associated with a low cGMP level.

Thus, the present invention relates to compounds of the formula I

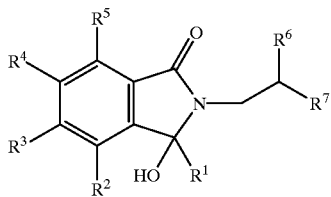

in which

R¹ is $(C_3-C_7)$-cycloalkyl, phenyl or the radical of a 5-membered or 6-membered aromatic heterocycle which contains one or two identical or different heteroatoms selected from the group consisting of N, O and S, where the phenyl radical and the heterocyclic radical are unsubstituted or substituted by one or more identical or different radicals selected from the group consisting of $(C_1-C_4)$-alkyl, halogen, hydroxyl, $(C_1-C_4)$-alkoxy, benzyloxy, phenoxy, benzyl, phenyl, trifluoromethyl, cyano, hydroxycarbonyl, $((C_1-C_4)$-alkoxy)carbonyl, aminocarbonyl, nitro, amino, $(C_1-C_4)$-alkylamino, di-$((C_1-C_4)$-alkyl)amino and $((C_1-C_4)$-alkyl)-carbonylamino;

R², R³, R⁴ and R⁵ independently of one another are hydrogen, halogen, $(C_1-C_4)$-alkyl or $(C_1-C_4)$-alkoxy;

R⁶ is phenyl which is unsubstituted or substituted by one or more identical or different radicals selected from the group consisting of $(C_1-C_4)$-alkyl, halogen, hydroxyl, $(C_1-C_4)$-alkoxy, benzyloxy, phenoxy, benzyl, phenyl, trifluoromethyl, cyano, hydroxycarbonyl, $((C_1-C_4)$-alkoxy)carbonyl, aminocarbonyl, nitro, amino, $(C_1-C_4)$-alkylamino, di-$((C_1-C_4)$-alkyl)amino and $((C_1-C_4)$-alkyl)carbonylamino;

R⁷ independently of R⁶ has one of the meanings of R⁶ or is hydrogen, in all their stereoisomeric forms and mixtures thereof in all ratios, and their physiologically acceptable salts;

where, if R¹ is unsubstituted phenyl and R², R³, R⁴, R⁵ and R⁷ are hydrogen, R⁶ may not simultaneously be unsubstituted phenyl or 3,4-dimethoxyphenyl.

Alkyl radicals may be straight-chain or branched. This also applies when they are part of other groups, for example of alkoxy groups. Examples of alkyl groups are methyl, ethyl, n-propyl, isopropyl, n-butyl, isobutyl, sec-butyl and tert-butyl. The term alkyl here also includes unsaturated alkyl radicals, in particular alkyl radicals which contain a double bond or a triple bond. Examples of such radicals are the vinyl radical, the 2-propenyl radical (allyl radical), the 2-butenyl radical, the 2-methyl-2-propenyl radical, the ethynyl radical, the 2-propynyl radical (propargyl radical) or the 3-butynyl radical.

Examples of cycloalkyl radicals are cyclopropyl, cyclobutyl, cyclopentyl, cyclohexyl and cycloheptyl, all of which may also be substituted, for example by one or more identical or different $(C_1-C_4)$-alkyl radicals, in particular by methyl. Examples of substituted cycloalkyl radicals are 4-methylcyclohexyl, 4-tert-butylcyclohexyl or 2,3-dimethylcyclopentyl.

Phenyl radicals may be unsubstituted or may carry one or more, for example two, three or four, identical or different substituents. The substituents can be in any positions. Preference is given to substituted phenyl radicals which are mono- or disubstituted. Monosubstituted phenyl radicals may be substituted in the 2-position, the 3-position or the 4-position, and in disubstituted phenyl radicals, the substituents can be located in the 2,3-position, 2,4-position, 2,5-position, 2,6-position, 3,4-position or 3,5-position. In trisubstituted phenyl radicals, the substituents can be located in the 2,3,4-position, the 2,3,5-position; 2,3,6-position, 2,4,5-position, 2,4,6-position or 3,4,5-position.

Examples of 5-membered and 6-membered aromatic heterocycles are furan, thiophene, pyrrole, pyrazole, imidazole, 1,3-oxazole, 1,3-thiazole, pyridine, pyridazine, pyrimidine and pyrazine. The radicals derived from these heterocycles may be attached via any carbon atom. A thienyl radical, for example, may be present as 2-thienyl radical or 3-thienyl radical, a furyl radical as 2-furyl radical or 3-furyl radical, a pyridyl radical as 2-pyridyl radical, 3-pyridyl radical or 4-pyridyl radical. The heterocycles may be unsubstituted or may carry one or more, for example two, three or four, identical or different substituents. Heterocyclic radicals are preferably unsubstituted or substituted by one or two identical or different radicals, in particular unsubstituted. The substituents in heterocycles can be in any positions, for example in a furyl radical or thienyl radical attached via the 2-position in the 3-position, the 4-position and/or the 5-position, in a furyl radical or thienyl radical attached via the 3-position in the 2-position, the 4-position and/or the 5-position, in a 2-pyridyl radical in the 3-position, the 4-position, the 5-position and/or the 6-position, in a 3-pyridyl radical in the 2-position, the 4-position, the 5-position and/or the 6-position, in a 4-pyridyl radical in the 2-position, the 3-position, the 5-position and/or the 6-position. Preferred substituents in heterocyclic radicals are $(C_1-C_4)$-alkyl radicals, in particular methyl, and/or halogen atoms, in particular chlorine and/or fluorine. Nitrogen heterocycles can also be present as N-oxides or as quaternary salts, pyridyl radicals for example as pyridine N-oxides.

If nitro groups are present as substituents in phenyl radicals and/or heterocyclic radicals, the total of nitro groups in the molecule of the compounds of the formula I may only be up to two. If phenyl radicals, phenoxy radicals, benzyl radicals or benzyloxy radicals are present as substituents in phenyl radicals and/or in heterocyclic radicals, the benzene ring in the former may for its part be unsubstituted or substituted by one or more, for example two, three or four, identical or different radicals from the group consisting of $(C_1-C_4)$-alkyl, halogen, hydroxyl, $(C_1-C_4)$-alkoxy, trifluoromethyl, cyano, hydroxycarbonyl, $((C_1-C_4)$-alkoxy) carbonyl, aminocarbonyl, nitro, amino, $(C_1-C_4)$-alkylamino, di-$((C_1-C_4)$-alkyl)amino and $((C_1-C_4)$-alkyl) carbonylamino.

Halogen is fluorine, chlorine, bromine or iodine, preferably fluorine or chlorine.

The present invention embraces all stereoisomeric forms of the compounds of the formula I. All centers of asymmetry contained in the compounds of the formula I may, independently of one another, have the S configuration or the R configuration. The invention includes all possible enantiomers and diastereomers, and also mixtures of two or more stereoisomeric forms, for example mixtures of enantiomers and/or diastereomers, in all ratios. Thus, the invention provides enantiomers in enantiomerically pure form, both as levorotatory and as dextrorotatory antipodes, in the form of racemates and in the form of mixtures of the two enantiomers in all ratios. In the case of a cis/trans isomerism, the invention provides both the cis form and the trans form and mixtures of these forms in all ratios. The preparation of individual stereoisomers can be carried out, if desired, by separation of a mixture by customary methods, for example by chromatography or crystallization, by the use of stereochemically uniform starting materials for the synthesis or by stereoselective synthesis. If appropriate, derivatization can be carried out prior to a separation of stereoisomers. The separation of a mixture of stereoisomers can be carried out at the stage of the compounds of the formula I or at the stage of an intermediate during the synthesis. If mobile hydrogen atoms are present, the present invention also includes all tautomeric forms of the compounds of the formula I. The invention furthermore also embraces all ring-chain tautomers of the compounds of the formula I, for example the compounds of the formula Ia.

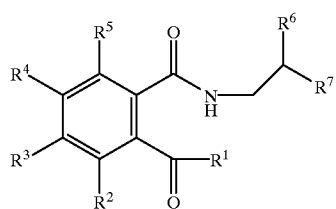

Ia

If the compounds of the formula I contain one or more acidic or basic groups, the invention also provides the corresponding physiologically or toxicologically acceptable salts, in particular the pharmaceutically utilizable salts. Thus, the compounds of the formula I which contain acidic groups may be present on these groups for example as alkali metal salts, alkaline earth metal salts or as ammonium salts, and may be used according to the invention as such salts. Examples of such salts are sodium salts, potassium salts, calcium salts, magnesium salts, salts with physiologically acceptable quaternary ammonium ions or acid addition salts with ammonia or physiologically acceptable organic amines, such as, for example, ethylamine, ethanolamine, triethanolamine or amino acids. Compounds of the formula I which contain one or more basic groups, i.e. groups which can be protonated, can be present, and can be used according to the invention, in the form of their acid addition salts with inorganic or organic acids, for example as salts with hydrogen chloride, hydrogen bromide, phosphoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, etc. If the compounds of the formula I simultaneously contain acidic and basic groups in the molecule, the invention also includes, in addition to the salt forms mentioned, inner salts or betaines. Salts can be obtained from the compounds of the formula I by customary methods which are known to the person skilled in the art, for example by combination with an organic or inorganic acid or base in a solvent or dispersant, or else by anion exchange or cation exchange from other salts. The present invention also includes all salts of the compounds of the formula I which, owing to low physiological compatibility, are not directly suitable for use in pharmaceuticals but which can be used, for example, as intermediates for chemical reactions or for the preparation of physiologically acceptable salts.

The present invention furthermore includes all solvates of compounds of the formula I, for example hydrates or adducts with alcohols, and also derivatives of the compounds of the formula I, for example esters, and prodrugs and active metabolites.

$R^1$ is preferably unsubstituted phenyl or phenyl which is substituted by one or two identical or different radicals selected from the group consisting of $(C_1-C_4)$-alkyl and halogen. Particularly preferably, $R^1$ is unsubstituted phenyl or phenyl which is substituted by one or two identical or different halogen atoms. Especially preferably, $R^1$ is unsubstituted phenyl or fluorophenyl, in particular 4-fluorophenyl.

$R^2$, $R^3$, $R^4$ and $R^5$ preferably independently of one another are hydrogen, halogen or $(C_1-C_4)$-alkyl, particularly preferably independently of one another are hydrogen, fluorine, chlorine or methyl. In an especially preferred embodiment, all radicals $R^2$, $R^3$, $R^4$ and $R^5$ are hydrogen.

$R^6$ is preferably phenyl which is unsubstituted or substituted by one or two identical or different radicals selected from the group consisting of $(C_1-C_4)$-alkyl, halogen and $(C_1-C_4)$-alkoxy, in particular in positions 2 and/or 3. Particularly preferably, $R^6$ is phenyl which is substituted by one or two identical or different radicals selected from the group consisting of halogen and $(C_1-C_4)$-alkoxy. Especially preferably, $R^6$ is methoxyphenyl, in particular 3-methoxyphenyl, or is chlorophenyl, in particular 2-chlorophenyl.

$R^7$ is preferably hydrogen.

Preferred compounds of the formula I are those in which one or more of the radicals contained therein have preferred meanings, all combinations of preferred substituent definitions being included. Also of all preferred compounds of the formula I the present invention includes all their stereoisomeric forms and mixtures thereof in all ratios, and their physiologically acceptable salts.

A group of preferred compounds of the formula I is formed by those compounds in which $R^1$ is unsubstituted phenyl or fluorophenyl, in particular 4-fluorophenyl; $R^2$, $R^3$, $R^4$ and $R^5$ are hydrogen; $R^6$ is methoxyphenyl, in particular 3-methoxyphenyl, or is chlorophenyl, in particular 2-chlorophenyl; $R^7$ is hydrogen; in all their stereoisomeric forms and mixtures thereof in all ratios, and their physiologically acceptable salts.

The present invention also provides processes for preparing the compounds of the formula I which are illustrated below and by which the compounds according to the invention are obtainable. The compounds can be prepared, for example, by reacting, analogously to Delcey et al., Heterocycles 41 (1995) 1721, benzoic acids of the formula II which are substituted in the 2-position by a keto group, or activated derivatives of the benzoic acids of the formula II, with primary amines of the formula III. In the formulae II and III, the radicals $R^1$, $R^2$, $R^3$, $R^4$, $R^5$, $R^6$ and $R^7$ are as defined above.

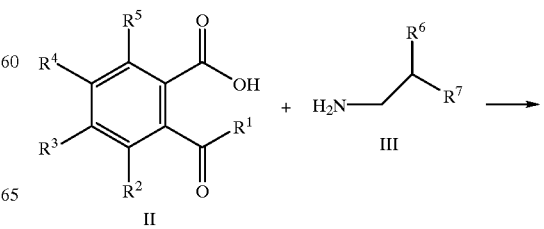

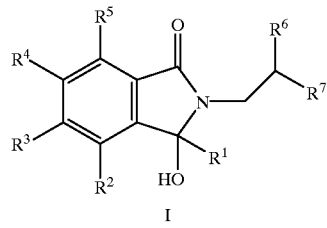

The 2-ketobenzoic acids of the formula II and the amines of the formula III used as starting materials are commercially available or can be prepared by or analogously to the standard processes described in the literature. If the carboxylic acid group in the compounds of the formula II is to be converted into an activated derivative of higher reactivity, this can be done by standard methods. For activation, the acid group can be converted, for example, into an ester, for example into an alkyl ester, such as a methyl ester or ethyl ester, or into an aryl ester, such as a phenyl ester, chlorophenyl ester or nitrophenyl ester, or it can be converted into an acyl halide, such as an acyl chloride or acyl bromide, or it can be converted into an azolide, for example using carbonyldiimidazole into an imidazolide, or it can be converted into a mixed anhydride, for example by reaction with an alkyl chloroformate. The activation of the carboxylic acid group for the reaction with the amine of the formula III can also be carried out, for example, using activating agents, such as carbodiimides or other reagents customarily used in peptide chemistry. The activation can be carried out in a separate step or in situ. A particularly simple and favorable method is the activation of carboxylic acids of the formula II, in particular those in which $R^1$ is an aromatic radical, for example a phenyl radical, by conversion into the carbonyl chlorides. This chlorination of benzoic acids to give the benzoyl chlorides can be carried out by standard methods for preparing acyl chlorides, for example using thionyl chloride, phosphorus chlorides or oxalyl dichloride in an inert solvent or dispersant or else in the absence of a solvent.

The reaction of compounds of the formula II or their activated derivatives with compounds of the formula III can be carried out by standard processes for reacting carboxylic acids or carboxylic acid derivatives with amines under reaction conditions which are well-known to the person skilled in the art. The reaction is preferably carried out in an inert solvent or dispersant. If, for example, according to a preferred variant of this preparation process, the acyl chloride of a compound of the formula II is used, the reaction is preferably carried out in an aprotic solvent or dispersant. In this case, suitable solvents or dispersants are, for example, ethers, such as diethyl ether, dipropyl ether, dibutyl ether, tert-butyl methyl ether, tetrahydrofuran, dioxane, ethylene glycol ethers and di- and triethylene glycol ethers, such as ethylene glycol dimethyl ether or diethylene glycol dimethyl ether, esters, such as ethyl acetate or butyl acetate, amides, such as dimethylformamide, dimethylacetamide, N-methylpyrrolidone or hexamethylphosphoric triamide, nitriles, such as acetonitrile, sulfoxides and sulfones, such as dimethyl sulfoxide or sulfolane, hydrocarbons and chlorinated hydrocarbons, such as petroleum fractions, benzene, toluene, xylene, chlorobenzene, dichlorobenzene, methylene chloride or chloroform. However, depending on the individual case and the derivative of the compound of the formula II employed, other solvents may also be suitable, for example water or alcohols, such as methanol, ethanol, n-propanol, isopropanol or butanols. In general, it is also possible to use mixtures of two or more solvents.

In particular in the preferred synthesis variant in which the acyl chloride of a compound of the formula II is used, the reaction is favorably carried out in the presence of a base, for example a tertiary amine, such as triethylamine, ethyldiisopropylamine, N-methylmorpholine or pyridine, which binds the hydrogen chloride that is formed.

The reactions of compounds of the formula II or their derivatives with compounds of the formula III to give compounds of the formula I are generally carried out between 0° C. and 140° C., preferably between room temperature and 140° C., and in the preferred variant using the acyl chloride of a compound of the formula II particularly preferably in the temperature range from 70° C. to 140° C. The duration of the reaction depends on the individual case; in general, the reaction is complete after 1 to 10 hours. The progress of the reaction can be monitored, for example, by chromatographic analysis of the reaction mixture. The resulting compounds of the formula I can be isolated from the reaction mixture by customary work-up processes, for example by extraction, and, if desired, be purified by customary purification methods, for example by crystallization, sublimation or by chromatography.

In a further process for preparing the compounds according to the invention, phthalimides of the formula IV are reacted with organometallic compounds of the formula V, for example with organolithium compounds or with Grignard compounds. In the formulae IV and V, the radicals $R^1$, $R^2$, $R^3$, $R^4$, $R^5$, $R^6$ and $R^7$ are as defined above and M is, for example, Li or MgCl, MgBr or MgI.

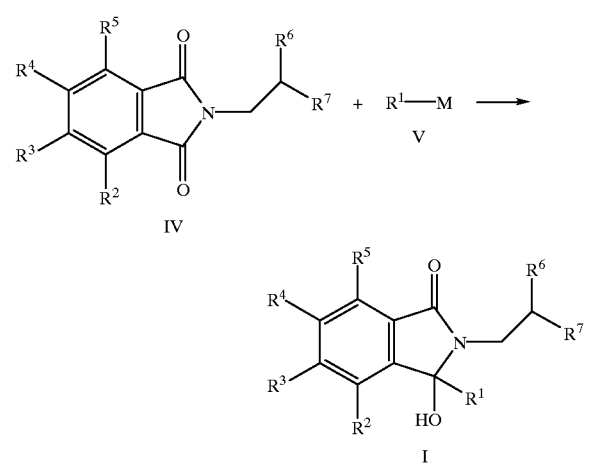

The starting materials of the formula IV can be prepared by or analogously to standard processes described in the literature, for example according to the specifications given by Bahajaj and Vernon, J. Chem. Soc. Perkin Trans. 1 (1996)1041, Boykin et al., J. Heterocycl. Chem. 28 (1991) 609 or Wanag, Chem. Ber. 75 (1942) 719. The organometallic compounds of the formula V are commercially available or can be prepared by methods which are well-known to the person skilled in the art, for example by reacting an organic halogen compound with a metal such as magnesium or lithium, or by transmetallation.

The reaction of the phthalimides of the formula IV with the organometallic compounds of the formula V is generally carried out in an inert solvent or dispersant. Preferred solvents or dispersants are ethers, such as diethyl ether, dipropyl ether, dibutyl ether, tert-butyl methyl ether, tetrahydrofuran, dioxane, ethylene glycol ethers and di- and triethylene glycol ethers, such as ethylene glycol dimethyl ether or diethylene glycol dimethyl ether. However, it is also possible to use other inert solvents, for example hydrocarbons, such as pentane, hexane, heptane, benzene or toluene. Likewise, it is possible to use mixtures of two or more solvents.

The reaction of the compounds of the formulae IV and V is generally carried out at temperatures from −75° C. to +80° C. The most favorable reaction temperature depends on the individual case, for example on the reactivity of the organometallic compound. In many cases, it is favorable to initially combine the reactants at a lower temperature, for example at approximately −70° C. or at approximately 0° C., and then to heat the reaction mixture to a higher temperature, for example room temperature or approximately 40° C., to bring the reaction to completion. As above, the resulting compounds of the formula I can be isolated from the reaction mixture by customary work-up processes, for example aqueous work-up with phase separation and/or extraction, and, if desired, be purified by customary purification methods, for example by crystallization, sublimation or by chromatography.

Depending on the circumstances of the individual case, it may be advantageous or necessary to use protective group techniques when preparing the compounds of the formula I by the processes mentioned. Which functional groups have to be temporarily protected, which protective groups are suitable for this purpose, and how to remove the protective groups is known to the person skilled in the art and described in standard works of organic chemistry, for example in Houben-Weyl, Methoden der Organischen Chemie [Methods of organic chemistry], Thieme-Verlag, Stuttgart, or Organic Reactions, John Wiley & Sons, New York. Acid groups, for example, can be protected by conversion into the benzyl esters, and the benzyl groups can later be cleaved off again by catalytic hydrogenation, or amino groups can be protected by acylation. It is also possible for functional groups to be initially present in the form of precursors which are then converted by standard methods into the desired groups after the synthesis of the molecular skeleton of the compounds of the formula I. A nitro group, for example, may serve as a precursor for an amino group.

The compounds of the formula I according to the invention effect an increase of the cGMP concentration via the activation of the soluble guanylate cyclase (sGC), and they are therefore useful agents for the therapy and prophylaxis of disorders which are associated with a low or decreased cGMP level or which are caused thereby, or for whose therapy or prophylaxis an increase in the present cGMP level is desired. The activation of the sGC by the compounds of the formula I can be examined, for example, in the activity assay described below.

Disorders and pathological conditions which are associated with a low cGMP level or in which an increase in the cGMP level is desired and for whose therapy and prophylaxis it is possible to use compounds of the formula I are, for example, cardiovascular diseases, such as endothelial dysfunction, diastolic dysfunction, atherosclerosis, hypertension, stable and unstable angina pectoris, thromboses, restenoses, myocardial infarction, strokes, coronary insufficiency or pulmonary hypertonia, or, for example, erectile dysfunction, bronchial asthma, chronic kidney insufficiency and diabetes. Compounds of the formula I can additionally be used in the therapy of cirrhosis of the liver and also for improving a restricted ability to learn or memory performance.

The compounds of the formula I and their physiologically acceptable salts can be administered to animals, preferably to mammals, and in particular to humans as pharmaceuticals by themselves, in mixtures with one another or in the form of pharmaceutical preparations. The present invention therefore also provides the compounds of the formula I and their physiologically acceptable salts for use as pharmaceuticals, their use for normalizing a disturbed cGMP balance and in particular their use in the therapy and prophylaxis of the abovementioned syndromes, and also their use for preparing medicaments for this purpose. Furthermore, the present invention provides pharmaceutical preparations which comprise as active component an effective dose of at least one compound of the formula I and/or a physiologically acceptable salt, and a customary pharmaceutically unobjectionable carrier. The present invention also provides the compounds of the formula I, already known as such, in which $R^1$ is unsubstituted phenyl, $R^2$, $R^3$, $R^4$, $R^5$ and $R^7$ are hydrogen and $R^6$ is unsubstituted phenyl or 3,4-dimethoxyphenyl, as activators of soluble guanylate cyclase. Everything stated above and below on the pharmacological action and the use of the compounds of the formula I also applies correspondingly to these two compounds; the invention thus also provides, for example, these compounds in all their stereoisomeric forms and mixtures thereof in all ratios and their physiologically acceptable salts for use as pharmaceuticals and pharmaceutical preparations which comprise as active component an effective dose of at least one of these compounds and/or a physiologically acceptable salt and a customary pharmaceutically unobjectionable carrier.

The pharmaceuticals can be administered orally, for example in the form of pills, tablets, lacquered tablets, sugar-coated tablets, granules, hard and soft gelatin capsules, aqueous, alcoholic or oily solutions, syrups, emulsions or suspensions, or rectally, for example in the form of suppositories. However, administration can also be carried out parenterally, for example subcutaneously, intramuscularly or intravenously in the form of solutions for injection or infusion. Other suitable administration forms are, for example, percutaneous or topical administration, for example in the form of ointments, tinctures, sprays or transdermal therapeutic systems, or the inhalative administration in the form of nasal sprays or aerosol mixtures, or, for example, microcapsules, implants or rods. The preferred administration form depends, for example, on the disease to be treated and on its severity.

The pharmaceutical preparations usually comprise 0.5 to 90 percent by weight of the compounds of the formula I and/or their physiologically acceptable salts. The preparation of the pharmaceutical preparations can be carried out in a manner known per se. For this purpose, one or more compounds of the formula I and/or their physiologically acceptable salts are brought into a suitable administration form or dosage form together with one or more solid or liquid pharmaceutical carrier substances and/or auxiliary substances and, if desired, in combination with other pharmaceutically active compounds having therapeutic or prophylactic action, which can then be used as a pharmaceutical in human or veterinary medicine. Pharmaceutical preparations normally contain 0.2 to 500 mg, preferably 1 to 200 mg, of active compound of the formula I and/or its physiologically acceptable salts per dose.

For the production of pills, tablets, sugar-coated tablets and hard gelatin capsules, it is possible to use, for example, lactose, starch, for example corn starch, or starch derivatives, talc, stearic acid or its salts, etc. Carrier substances for soft gelatin capsules and suppositories are, for example, fats, waxes, semisolid and liquid polyols, natural or hardened oils, etc. Suitable carrier substances for the preparation of solutions, for example of solutions for injection, or of emulsions or syrups are, for example, water, saline, alcohols such as ethanol, glycerol, polyols, sucrose, invert sugar, glucose, mannitol, vegetable oils, etc. It is also possible to lyophilize the compounds of the formula I and their physiologically acceptable salts and to use the resulting lyophilizates, for example, for producing preparations for injection or infusion. Suitable carrier substances for microcapsules, implants or rods are, for example, copolymers of glycolic acid and lactic acid.

Besides the active compounds and carrier substances, the pharmaceutical preparations of the invention can also contain customary additives, for example fillers, disintegrants, binders, lubricants, wetting agents, stabilizers, emulsifiers, dispersants, preservatives, sweeteners, colorants, flavorings or aromatizers, thickeners, diluents, buffer substances, furthermore solvents or solubilizers or agents for achieving a depot effect, and salts for altering the osmotic pressure, coating agents or antioxidants.

The dosage of the active compound of the formula I to be administered and/or of a physiologically acceptable salt thereof depends on the individual case and is, as is customary, to be adapted to the individual circumstances to achieve an optimum effect. Thus, it depends on the nature and the severity of the disorder to be treated, and also on the sex, age, weight and individual responsiveness of the human or animal to be treated, on the efficacy and duration of action of the compounds used, on whether the therapy is acute or chronic or prophylactic, or on whether other active compounds are administered in addition to compounds of the formula I. In general, a daily dose of approximately 0.01 to 100 mg/kg, preferably 0.1 to 10 mg/kg, in particular 0.3 to 5 mg/kg (in each case mg per kg of bodyweight) is appropriate for administration to an adult weighing approximately 75 kg in order to obtain effective results. The daily dose can be administered in a single dose or, in particular when larger amounts are administered, be divided into several, for example two, three or four individual doses. In some cases, depending on the individual response, it may be necessary to deviate upward or downward from the given daily dose.

The compounds of the formula I activate the soluble guanylate cyclase. On account of this property, apart from use as pharmaceutically active compounds in human medicine and veterinary medicine, they can also be employed as a scientific tool or as aids for biochemical investigations in which such an effect on guanylate cyclase is intended, and also for diagnostic purposes, for example in the in vitro diagnosis of cell or tissue samples. The compounds of the formula I and salts thereof can furthermore be employed, as already mentioned above, as intermediates for the synthesis of other, in particular pharmaceutically active, compounds.

The following examples illustrate the invention, without limiting it.

EXAMPLE 1

2-(2-(2-Fluorophenyl)ethyl)-3-hydroxy-3-phenyl-2,3-dihydroisoindol-1-one

At room temperature, 0.31 g (2.2 mmol) of 2-(2-fluorophenyl)ethylamine and 0.22 g (2.2 mmol) of triethylamine in 10 ml of absolute toluene were admixed dropwise with a solution of 0.49 g (2.0 mmol) of 2-benzoylbenzoyl chloride in 10 ml of absolute toluene. The reaction mixture was heated under eflux for 3 h. After cooling, the turbid solution was admixed with 20 ml of water. The organic phase was separated off, diluted with 20 ml of toluene and washed three times with 1 M hydrochloric acid. To complete the extraction, the combined aqueous phases were extracted with diethyl ether. The combined organic phases were washed three times with 1 M aqueous sodium hydroxide solution and once with saturated sodium chloride solution, dried over sodium sulfate and evaporated to dryness using a rotary evaporator. The residue was recrystallized from toluene. The resulting colorless crystalline product was filtered off with suction and dried. Yield: 53 g. M.p.: 208° C.

The following compounds of the formula Ib listed in Table 1 were prepared analogously to Example 1 using the corresponding amine.

TABLE 1

Example compounds of the formula Ib

Ib

| Example | $R^6$ | Yield (%) | M.p. (° C.) |
|---|---|---|---|
| 2 | 2,4-dichlorophenyl | 65 | 196 |
| 3 | 2-methoxyphenyl | 82 | 151 |
| 4 | 3-fluorophenyl | 72 | 158 |
| 5 | 4-fluorophenyl | 90 | 156 |
| 6 | 3-chlorophenyl | 40 | 110 |
| 7 | 4-methylphenyl | 100 | 144 |
| 8 | 4-phenoxyphenyl | 76 | 144 |
| 9 | 3,4-dichlorophenyl | 51 | 150 |
| 10 | 2,3-dimethoxyphenyl | 79 | 171 |
| 11 | 3-methoxyphenyl | 82 | 118 |
| 12 | 2-chlorophenyl | 87 | 201 |
| 13 | 3-trifluoromethylphenyl | 73 | 110 |
| 14 | 4-chlorophenyl | 70 | 165 |

EXAMPLE 15

2-(2-(2,2-Diphenylethyl)-3-hydroxy-3-phenyl-2,3-dihydroisoindol-1-one

This compound was prepared analogously to Example 1 using 2,2-diphenylethylamine. Yield: 32%. M.p.: 230° C.

EXAMPLE 16

3-Hydroxy-2-(2-(4-hydroxyphenyl)ethyl)-3-phenyl-2,3-dihydroisoindol-1-one

At room temperature, 1.46 g (10.63 mmol) of 2-(4-hydroxy-phenyl)ethylamine and 1.08 g (10.63 mmol) of triethylamine in 30 ml of absolute toluene were admixed dropwise with a solution of 2.0 g (8.17 mmol) of 2-benzoylbenzoyl chloride in 20 ml of absolute toluene. The reaction mixture was heated under reflux for 3 h and cooled, and the turbid solution was admixed with 20 ml of water. The organic phase was separated off, washed three times with 1 M aqueous hydrochloric acid and evaporated to dryness using a rotary evaporator. The solid residue was purified by column chromatography on silica gel 60. Elution was carried out using a toluene/ethyl acetate gradient (0 to 20% ethyl acetate). The product-containing fractions were evaporated to dryness using a rotary evaporator. The residue was suspended in diethyl ether and filtered off with suction. Yield: 0.21 g. M.p.: 188° C.

EXAMPLE 17

3-(4-Fluorophenyl)-3-hydroxy-2-(2-(3-methoxyphenyl)ethyl)-2,3-dihydro-isoindol-1-one At 0° C. and under protective gas, 2.0 g (7.11 mol) of N-(2-(3-methoxyphenyl)ethyl)phthalimide in 30 ml of absolute tetrahydrofuran were admixed with 5.37 g (14.22 mmol) of a 1 M solution of 4-fluorophenylmagnesium bromide in diethyl ether. The reaction mixture was allowed to warm to room temperature and, after 3 h, admixed with 20 ml of saturated sodium bicarbonate solution. The aqueous phase was extracted twice with diethyl ether. The combined organic phases were dried and evaporated to dryness using a rotary evaporator. The solid residue was recrystallized from toluene. This gave colorless needles. Yield: 2.21 g. M.p.:134° C.

The following compounds of the formula Ic listed in Table 2 were prepared analogously to Example 17 using the corresponding phthalimide and the corresponding Grignard reagent. Purification was carried out as stated in Table 2.

The aqueous phase was extracted twice with diethyl ether. The combined organic phases were dried and evaporated to dryness using a rotary evaporator. The resulting oil was purified by chromatography. Elution was carried out using a dichloromethanelmethanol gradient (0 to 2% methanol). The product, obtained as a colorless oils was foamed by coevaporation with diethyl ether. Yield: 0.32 g. M.p.: 119° C.

EXAMPLE 28

3-Hydroxy-2-(2-(3-methoxyphenyl)ethyl)-3-(4-trifluoromethylphenyl)-2,3-dihydroisoindol-1-one At room temperature, 172 mg (7.08 mmol) of magnesium turnings in 10 ml of absolute diethyl ether were admixed with 1.6 g (7.11 mmol) of 4-trifluoromethylbromobenzene. The reaction was started by addition of a drop of bromine. After about 2 h, the magnesium had completely dissolved. The mixture was cooled to 0° C. and 0.5 g (1.78 mmol) of N-(2-(3-methoxyphenyl)ethyl)phthalimide was added. The reaction mixture was allowed to warm to room temperature

TABLE 2

Example compounds of the formula Ic

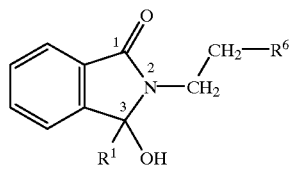

Ic

| Example | $R^6$ | $R^1$ | Purification (solvent) | Yield (%) | M.p. (° C.) |
|---|---|---|---|---|---|
| 18 | 3-hydroxyphenyl | phenyl | chromatography | 52 | 149 |
| 19 | 2-chlorophenyl | 4-methylphenyl | crystallization (1) | 71 | 182 |
| 20 | 2-chlorophenyl | cyclopentyl | foamed (2) | 51 | 52 |
| 21 | 3-methoxyphenyl | 3-methylphenyl | chromatography | 88 | oil |
| 22 | 3-methoxyphenyl | 2-methylphenyl | chromatography, crystallization (2) | 23 | 128 |
| 23 | 3-methoxyphenyl | 4-methylphenyl | chromatography, crystallization (3) | 53 | 84 |
| 24 | 3-methoxyphenyl | 4-chlorophenyl | chromatography, crystallization (3) | 60 | 106 |
| 25 | 3-methoxyphenyl | cyclohexyl | chromatography | 87 | oil |
| 26 | 3-methoxyphenyl | cyclopentyl | chromatography, crystallization (4) | 47 | 102 |

The meaning of the solvents as indicated in Table 2 is: (1): from diethyl ether/tert-butyl methyl ether; (2): from diethyl ether; (3): from diisopropyl ether; (4): from n-heptane/diethyl ether

EXAMPLE 27

3-Hydroxy-3-(4-methoxyphenyl)-2-(2-(3-methoxyphenyl)ethyl)-2,3-dihydro-isoindol-1-one 104 mg (4.28 mmol) of magnesium turnings in 10 ml of absolute diethyl ether were admixed with 0.79 g (4.27 mmol) of 4-bromoanisole. The reaction was started by addition of a drop of bromine. After about 2 h, the magnesium had completely dissolved. The mixture was cooled to 0° C. and 0.3 g (1.07 mmol) of N-(2-(3-methoxyphenyl) ethyl)phthalimide was added. The reaction mixture was allowed to warm to room temperature and, after 2 h, admixed with 5 ml of saturated sodium bicarbonate solution.

and, after 2 h, admixed with 5 ml of saturated sodium bicarbonate solution. The aqueous phase was extracted twice with diethyl ether. The combined organic phases were dried and evaporated to dryness using a rotary evaporator. The red crystalline residue was recrystallized from toluene. This gave a colorless product. Yield: 0.49 g. M.p.: 167° C.

EXAMPLE 29

3-Hydroxy-2-(2-(3-methoxyphenyl)ethyl)-3-(4pyridyl)-2,3-dihydroisoindol-1-one 0.69 g (3.55 mmol) of 4-bromopyridine hydrochloride was initially converted into the free base. To this end, the salt was dissolved in 5 ml of 1 M aqueous sodium hydroxide solution, the solution was extracted three times with diethyl ether and the combined organic phases were dried and evaporated to dryness using a rotary evaporator. The residue was dissolved in 5 ml of absolute diethyl ether and the solution was added dropwise at −70° C. to a mixture of 1.6 M butyllithium solution in n-hexane (3.98 mmol) and 10 ml of absolute diethyl ether. The mixture was stirred at −70° C. for 30 min, and a solution of 0.5 g (1.78 mmol) of N-(2-(3-methoxyphenyl)ethyl)phthalimide in 10 ml of absolute tetrahydrofuran was then added dropwise (color change from yellow to brown). After 1 h, the reaction mixture was allowed to warm to room temperature, admixed with 10 ml of saturated ammonium chloride solution and extracted three times with diethyl ether. The combined organic phases were washed once with saturated sodium chloride solution, dried and evaporated to dryness using a rotary evaporator. Recrystallization of the crystalline residue from diisopropyl ether/ethanol gave a colorless crystalline product. Yield: 0.28 g. M.p.: 190° C.

EXAMPLE 30

3-Hydroxy-2-(2-(3-methoxyphenyl)ethyl)-3-(3-pyridyl)-2,3-dihydroisoindol-1-one

At −70° C., a 1.6 M butyllithium solution (3.99 mmol) in absolute diethyl ether was admixed dropwise with a solution of 0.56 g (3.56 mmol) of 3-bromopyridine in absolute diethyl ether. The color of the mixture changed to yellow, and a precipitate was formed. After 1 h at −70° C., a solution of 0.5 g (1.78 mmol) of N-(2-(3-methoxyphenyl)ethyl) phthalimide in 10 ml of absolute tetrahydrofuran was added dropwise. The reaction mixture was warmed to room temperature, stirred for another 1 h and then admixed with 10 ml of saturated ammonium chloride solution. The mixture was extracted three times with diethyl ether. The combined organic phases were washed once with saturated sodium chloride solution, dried and evaporated to dryness using a rotary evaporator. The colorless oily crude product was purified by chromatography. Elution was carried out using a dichloromethane/methanol gradient (0 to 3% methanol). The resulting colorless oil solidified on standing at room temperature. Yield: 0.34 g. M.p.: 97° C.

EXAMPLE 31

3-Hydroxy-2-(2-(3-methoxyphenyl)ethyl)-3-(2-thienyl)-2,3-dihydroisoindol-1-one 0.3 g (1.07 mmol) of N-(2-(3-methoxyphenyl)ethyl) phthalimide was dissolved in 10 ml of absolute tetrahydrofuran and, at 0° C., admixed dropwise with a 1 M solution of 0.14 g (1.6 mmol) of 2-thienyllithium. The reaction mixture was allowed to warm to room temperature, after which stirring was continued for 2 h, and the mixture was then admixed with 10 ml of saturated ammonium chloride solution. The mixture was extracted three times with diethyl ether and the combined organic phases were washed once with saturated sodium chloride solution, dried and evaporated to dryness using a rotary evaporator. The oily crude product was purified by chromatography. Elution was carried out using a dichloromethanelmethanol gradient (0 to 1% methanol). Yield: 0.2 g of an oil.

EXAMPLE 32

5,6-Dichloro-3-(4-fluorophenyl)-3-hydroxy-2-(2-(3-methoxyphenyl)ethyl)-2,3-dihydroisoindol-1-one 0.4 g (1.14 mmol) of 4,5-dichloro-N-(3-methoxyphenyl) ethyl)phthalimide was dissolved in 10 ml of absolute tetrahydrofuran and, at 0° C., admixed with a 1 M solution of 4-fluorophenylmagnesium bromide (1.71 mmol) in tetrahydrofuran. The mixture was stirred at room temperature for 3 h, and once again a 1 M solution of 4-fluorophenylmagnesium bromide (1 mmol) in tetrahydrofuran was added. After 1 h, the reaction mixture was admixed with 10 ml of saturated ammonium chloride solution. The organic phase was separated off and the aqueous phase was extracted three times with diethyl ether. The combined organic phases were washed with saturated sodium chloride solution, dried and evaporated to dryness using a rotary evaporator. The colorless residue was suspended in diethyl ether and filtered off with suction. Yield: 0.13 g. M.p.: 169° C.

EXAMPLE 33

4,5,6,7-Tetrafluoro-3-(4-fluorophenyl)-3-hydroxy-2-(2-(3-methoxyphenyl)-ethyl)-2,3-dihydroisoindol-1-one 0.4 g (1.13 mmol) of 3,4,5,6-tetrafluoro-N-(3-methoxyphenyl)-ethyl)phthalimide was dissolved in 10 ml of absolute tetrahydrofuran and, at 0° C., admixed with a 1 M solution of 4-fluorophenylmagnesium bromide (2.3 mmol) in tetrahydrofuran. The reaction mixture was stirred at room temperature for 3 h and then admixed with 10 ml of saturated ammonium chloride solution, the organic phase was separated off and the aqueous phase was extracted three times with diethyl ether. The combined organic phases were washed with saturated sodium chloride solution, dried and evaporated to dryness using a rotary evaporator. The colorless residue was recrystallized from toluene. Yield: 0.32 9. M.p.: 161° C.

EXAMPLE 34

4,7-Difluoro-3-(4-fluorophenyl)-3-hydroxy-2-(2-(3-methoxyphenyl)ethyl-2,3-dihydroisoindol-1-one 0.25 g (0.79 mmol) of 3,6-difluoro-N-(3-methoxyphenyl) ethyl)phthalimide was dissolved in 10 ml of absolute tetrahydrofuran and, at 0° C., admixed with a 1 M solution of 0.31 g (1.58 mmol) of 4-fluorophenylmagnesium bromide in tetrahydrofuran. The reaction mixture was stirred at room temperature for 3 h and then admixed with 10 ml of saturated ammonium chloride solution, the organic phase was separated off and the aqueous phase was extracted three times with diethyl ether. The combined organic phases were washed with saturated sodium chloride solution, dried and evaporated to dryness using a rotary evaporator. The colorless residue was suspended in diethyl ether and filtered off with suction. Yield: 0.19 g. M.p.: 152° C.

EXAMPLE 35

4,7-Difluoro-3-hydroxy-2-(2-(3-methoxyphenyl) ethyl)-3-phenyl-2,3-dihydro-isoindol-1-one 0.17 g (0.53 mmol) of 3,6-difluoro-N-(3-methoxyphenyl) ethyl)phthalimide was dissolved in 5 ml of absolute tetrahydrofuran and, at 0° C., admixed with a 1 M solution of 0.19 g (1.07 mmol) of phenylmagnesium bromide in tetrahydrofuran. The reaction mixture was stirred at room temperature for 3 h and then admixed with 5 ml of saturated ammonium chloride solution, the organic phase was separated off and the aqueous phase was extracted three times with diethyl ether. The combined organic phases were washed with saturated sodium chloride solution, dried and evaporated to dryness using a rotary evaporator. The colorless residue was suspended in diethyl ether and filtered off with suction. Yield: 0.085 g. M.p.: 141° C.

EXAMPLE 36

3-(4-Fluorophenyl)-3-hydroxy-2-(2-(3-methoxyphenyl)ethyl)-4,5,6,7-tetra-methyl-2,3-dihydroisoindol-1-one 0.23 g (0.68 mmol) of N-(3-methoxyphenyl)ethyl)-3,4,5,6-tetramethyl-phthalimide was dissolved in 5 ml of absolute tetrahydrofuran and, at 0° C., admixed with a 1 M solution of 0.27 g (1.36 mmol) of 4-fluorophenylmagnesium bromide in tetrahydrofuran. The mixture was stirred at room temperature for 3 h, after which once more a 1 M solution of 4-fluorophenylmagnesium bromide (2 mmol) in tetrahydrofuran was added. The reaction mixture was stirred at room temperature for 1 h and then admixed with 5 ml of saturated ammonium chloride solution. The organic phase was separated off and the aqueous phase was extracted three times with diethyl ether. The combined organic phases were washed with saturated sodium chloride solution, dried and evaporated to dryness using a rotary evaporator. The oily residue was recrystallized from diisopropyl ether. Yield: 0.18 9. M.p.: 181° C.

Pharmacological Investigations

Activation of the Soluble Guanylate Cyclase

The activation of the soluble guanylate cyclase (sGC), which catalyzes the conversion of guanosine triphosphate (GTP) into cyclic guanosine monophosphate (cGMP) and pyrophosphate, by the compounds according to the invention was quantified with the aid of an enzyme immunoassay (EIA) from Amersham. To this end, the substances to be tested were initially incubated with sGC in microtiter plates, and the amount of the cGMP formed was then determined.

The sGC which was employed had been isolated from bovine lung (see Methods in Enzymology, volume 195, p. 377). The test solutions (100 μl per well) contained 50 mM triethanolamine (TEA) buffer (pH 7.5), 3 mM $MgCl_2$, 3 mM reduced glutathione (GSH), 0.1 mM GTP, 1 mM 3-isobutyl-1-methylxanthine (IBMX), suitably diluted enzyme solution and the substance to be tested or, in control experiments, the solvent. The substances to be tested were dissolved in dimethyl sulfoxide (DMSO) and the solution was diluted with DMSO/water, so that the final concentration of the substance to be tested in the test mixture was 50 μM. The DMSO concentration in the test mixture was 5% (v/v). The reaction was initiated by addition of the sGC. The reaction mixture was incubated at 37° C. for 15 to 20 minutes and the reaction was then stopped by ice-cooling and addition of the stop reagent (50 mM EDTA, pH 8.0). An aliquot of 50 μl was taken and used for determining the cGMP content using the acetylation protocol of the Amersham cGMP-EIA kit. The absorption of the samples was measured at 450 nm (reference wavelength 620 nm) in a microtiter plate reader. The cGMP concentration was determined using a standard curve which was obtained under the same test conditions. The activation of sGC by a test substance is reported as the n-fold stimulation of the basal enzyme activity which was found in the control experiments (using solvent instead of test substance) (calculated using the formula n-fold stimulation=$[cGMP]_{test\ substance}/[cGMP]_{control}$).

The following values were determined:

| Compound | Concentration | n-fold stimulation |
|---|---|---|
| Example 11 | 100 μM | 23.5-fold |
| Example 17 | 50 μM | 16-fold |
| Example 20 | 50 μM | 8.2-fold |
| Example 29 | 50 μM | 11.8-fold |
| Example 33 | 50 μM | 9.5-fold |
| A (comparison) | 50 μM | 2-fold |

Compound A, which was tested by way of comparison, is 1-benzyl-3-(5-hydroxymethyl-2-furyl)-indazole (C.-C. Wu et al., Brit. J. Pharmacol. 116 (1995) 1973).

What is claimed is:

1. A compound of the formula I

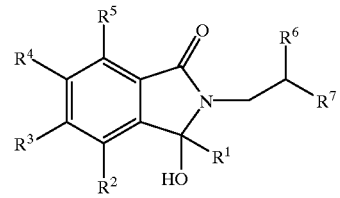

in which $R^1$ is ($C_3$–$C_7$)-cycloalkyl, phenyl or the radical of a 5-membered or 6-membered aromatic heterocycle which contains one or two identical or different heteroatoms selected from the group consisting of N, O and S, where the phenyl radical and the heterocyclic radical are unsubstituted or substituted by one or more identical or different radicals selected from the group consisting of ($C_1$–$C_4$)-alkyl, halogen, hydroxyl, ($C_1$–$C_4$)-alkoxy, benzyloxy, phenoxy, benzyl, phenyl, trifluoromethyl, cyano, hydroxycarbonyl, (($C_1$–$C_4$)-alkoxy)carbonyl, aminocarbonyl, nitro, amino, ($C_1$–$C_4$)-alkylamino, di-(($C_1$–$C_4$)-alkyl)amino and (($C_1$–$C_4$)-alkyl)carbonylamino;

$R^2$, $R^3$, $R^4$ and $R^5$ independently of one another are hydrogen, halogen, ($C_1$–$C_4$)-alkyl or ($C_1$–$C_4$)-alkoxy;

$R^6$ is phenyl which is unsubstituted or substituted by one or more identical or different radicals selected from the group consisting of ($C_1$–$C_4$)-alkyl, halogen, hydroxyl, ($C_1$–$C_4$)-alkoxy, benzyloxy, phenoxy, benzyl, phenyl, trifluoromethyl, cyano, hydroxycarbonyl, (($C_1$–$C_4$)-alkoxy)carbonyl, aminocarbonyl, nitro, amino, ($C_1$–$C_4$)-alkylamino, di-(($C_1$–$C_4$)-alkyl)amino and (($C_1$–$C_4$)-alkyl)carbonylamino;

$R^7$ independently of $R^6$ has one of the meanings of $R^6$ or is hydrogen, in any stereoisomeric form, or a physiologically acceptable salt thereof, or a mixture of compounds and/or salts thereof;

where, if $R^1$ is unsubstituted phenyl and $R^2$, $R^3$, $R^4$, $R^5$ and $R^7$ are hydrogen, $R^6$ may not simultaneously be unsubstituted phenyl or 3,4-dimethoxyphenyl.

2. A compound or mixture as claimed in claim 1 in which $R^1$ is unsubstituted phenyl or phenyl which is substituted by one or two identical or different radicals selected from the group consisting of ($C_1$–$C_4$)-alkyl and halogen.

3. A compound or mixture as claimed in claim 1 in which $R^2$, $R^3$, $R^4$ and $R^5$ independently of one another are hydrogen, fluorine, chlorine or methyl.

4. A compound or mixture as claimed in claim 1 in which $R^6$ is phenyl which is unsubstituted or substituted by one or two identical or different radicals selected from the group consisting of $(C_1-C_4)$-alkyl, halogen and $(C_1-C_4)$-alkoxy.

5. A compound or mixture as claimed in claim 1 in which $R^6$ is phenyl which is substituted by one or two identical or different radicals selected from the group consisting of halogen and $(C_1-C_4)$-alkoxy.

6. A compound or mixture as claimed in claim 1 in which $R^7$ is hydrogen.

7. A compound or mixture as claimed in claim 1 in which $R^1$ is unsubstituted phenyl or fluorophenyl;

$R^2$, $R^3$, $R^4$ and $R^5$ are hydrogen;

$R^6$ is methoxyphenyl or chlorophenyl; and $R^7$ is hydrogen.

8. A process for preparing a compound of the formula I as claimed in claim 1, which comprises reacting a benzoic acid of the formula II or an activated derivative thereof with an amine of the formula III

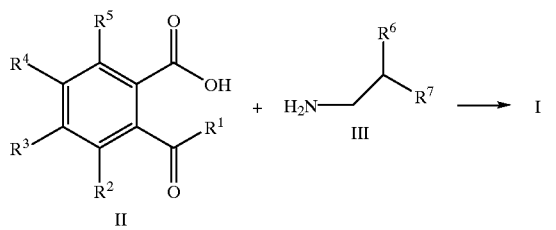

or reacting a phthalimide of the formula IV with an organometallic compound of the formula V

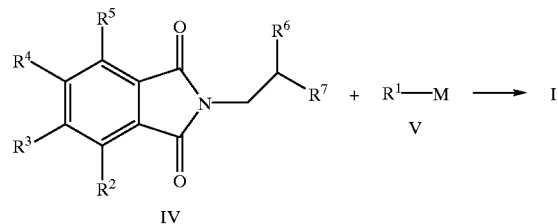

where in the formulae II, III, IV and V the radicals $R^1$, $R^2$, $R^3$, $R^4$, $R^5$, $R^6$ and $R^7$ are as defined in claim 1 and M is Li or MgCl, MgBr or MgI.

9. A pharmaceutical preparation, which comprises one or more compounds as claimed in claim 1 and a pharmaceutically unobjectionable carrier.

10. A method for the activation of soluble guanylate cyclase, which comprises administering to a host in need of the activation an effective amount of a compound or mixture as claimed in claim 1.

11. A method for the therapy or prophylaxis of a cardiovascular disease, which comprises administering to a host in need of the therapy or prophylaxis an effective amount of a compound or mixture as claimed in claim 1.

12. A method as claimed in claim 11, wherein the cardiovascular disease is endothelial dysfunction, diastolic dysfunction, atherosclerosis, hypertension,, angina pectoris, thrombosis, restenosis, myocardial infarction, stroke, cardiac insufficiency, or pulmonary hypertonia.

13. A method for the therapy or prophylaxis of erectile dysfunction, bronchial asthma, chronic kidney insufficiency, diabetes, or cirrhosis of the liver, which comprises administering to a host in need of the therapy or prophylaxis an effective amount of a compound or mixture as claimed in claim 1.

14. A method for improving a restricted ability to learn or memory performance, which comprises administering to a host in need of the improvement an effective amount of a compound or mixture as claimed in claim 1.

* * * * *